(12) United States Patent
Takeuchi et al.

(10) Patent No.: US 10,218,038 B2
(45) Date of Patent: Feb. 26, 2019

(54) BATTERY SENSOR POSITIONER, BATTERY SENSOR ASSEMBLY EQUIPPED WITH SAME, AND BATTERY SENSOR

(71) Applicants: FURUKAWA ELECTRIC CO., LTD., Tokyo (JP); FURUKAWA AUTOMOTIVE SYSTEMS INC., Shiga (JP); HONDA MOTOR CO., LTD., Tokyo (JP)

(72) Inventors: Haruhiko Takeuchi, Shiga (JP); Kazuyuki Tanaka, Shiga (JP); Nobuhiro Kondo, Saitama (JP); Daiki Abe, Saitama (JP)

(73) Assignees: FURUKAWA ELECTRIC CO., LTD., Tokyo (JP); FURUKAWA AUTOMOTIVE SYSTEMS INC., Shiga (JP); HONDA MOTOR CO., LTD., Tokyo (JP)

( * ) Notice: Subject to any disclaimer, the term of this patent is extended or adjusted under 35 U.S.C. 154(b) by 521 days.

(21) Appl. No.: 14/965,827

(22) Filed: Dec. 10, 2015

(65) Prior Publication Data
US 2016/0099487 A1 Apr. 7, 2016

Related U.S. Application Data (63) Continuation of application No. PCT/JP2014/002809, filed on May 28, 2014.

(30) Foreign Application Priority Data

Jun. 11, 2013 (JP) .................................. 2013-122869

(51) Int. Cl.
G01N 27/416 (2006.01)
H01M 10/48 (2006.01)
(Continued)

(52) U.S. Cl.
CPC ........ *H01M 10/48* (2013.01); *G01R 31/3606* (2013.01); *G01R 31/3644* (2013.01);
(Continued)

(58) Field of Classification Search
CPC ..... G01R 31/3658; G01N 31/02; G01N 27/42
(Continued)

(56) References Cited

U.S. PATENT DOCUMENTS

| 6,034,614 A * | 3/2000 | Haley ....................... G01V 1/16 |
| | | 200/61.45 R |
| 2002/0051906 A1* | 5/2002 | Wakata .............. G01R 31/3696 |
| | | 429/178 |

(Continued)

FOREIGN PATENT DOCUMENTS

| JP | 2002-280083 A | 9/2002 |
| JP | 2010-505103 A | 2/2010 |

(Continued)

OTHER PUBLICATIONS

JP 2011-175884 Machine Translation, Sep. 8, 2011.*
(Continued)

*Primary Examiner* — Huy Q Phan
*Assistant Examiner* — Raul Rios Russo
(74) *Attorney, Agent, or Firm* — Amin, Turocy & Watson, LLP (57) ABSTRACT

A battery sensor assembly (10) is provided with a positioner (11) and a battery sensor (1). The positioner (11) is provided with a sensor-fixing part (29) for fixing the battery sensor (1) and a rotation-blocking part (31) capable of coming in contact with a side surface (2*b*) of a battery (2). The sensor-fixing part (29) is provided with a fitting section (30). The fitting section (30) allows a casing (8) of the battery sensor (1) to be inserted from a prescribed insertion direction and fits to the inserted battery sensor (1). Additionally,
(Continued)

the rotation-blocking part (31) is provided with a reinforcement rib.

7 Claims, 9 Drawing Sheets

(51) Int. Cl.
  *G01R 31/36* (2019.01)
  *H01M 2/30* (2006.01)
  *G01N 27/42* (2006.01)
  *G01N 31/02* (2006.01)

(52) U.S. Cl.
  CPC ........ *G01R 31/3658* (2013.01); *H01M 2/305* (2013.01); *G01N 27/42* (2013.01); *G01N 31/02* (2013.01); *H01M 2220/20* (2013.01)

(58) Field of Classification Search
  USPC .................................................. 324/425–437
  See application file for complete search history.

(56) References Cited

U.S. PATENT DOCUMENTS

| | | | |
|---|---|---|---|
| 2009/0243622 A1 | 10/2009 | Schimmel | |
| 2010/0055994 A1* | 3/2010 | Mizutani | H01M 2/206 439/764 |
| 2012/0126818 A1* | 5/2012 | Ishihara | G01R 31/3696 324/426 |
| 2013/0136971 A1* | 5/2013 | Igarashi | H01M 2/1072 429/99 |
| 2013/0216883 A1* | 8/2013 | Kawatani | H01M 2/305 429/99 |
| 2013/0252050 A1 | 9/2013 | Uematsu | |

FOREIGN PATENT DOCUMENTS

| | | |
|---|---|---|
| JP | 2010160990 A | 7/2010 |
| JP | 2011175884 A | 9/2011 |
| JP | 2011181191 A | 9/2011 |
| JP | 2012-109098 A | 6/2012 |
| JP | 2012-109099 A | 6/2012 |

OTHER PUBLICATIONS

JP 2011-181191 Machine Translation, Sep. 15, 2011.*
International Search Report for PCT Application Serial No. PCT/JP2014/002809, dated Jul. 1, 2014, 2 pages.

* cited by examiner

PRIOR ART

Fig.9

PRIOR ART

BATTERY SENSOR POSITIONER, BATTERY SENSOR ASSEMBLY EQUIPPED WITH SAME, AND BATTERY SENSOR

CROSS-REFERENCE TO RELATED APPLICATION

The subject application is a continuation of, and claims priority to, PCT Application Ser. No. PCT/JP2014/002809, filed May 28, 2014, and entitled "BATTERY SENSOR POSITIONER, BATTERY SENSOR ASSEMBLY EQUIPPED WITH SAME, AND BATTERY SENSOR", which claims priority to Japanese Patent Application Serial No. 2013-122869, filed Jun. 11, 2013, the disclosures of which are incorporated herein by reference in their entirely.

TECHNICAL FIELD

The present invention mainly relates to a structure in a position settlement of a battery sensor.

BACKGROUND ART

Conventionally used is a battery sensor for detecting the state of a battery in the field of vehicles or the like. The battery sensor of this type is disclosed in, for example, Patent Documents 1 to 4.

Figure 8:
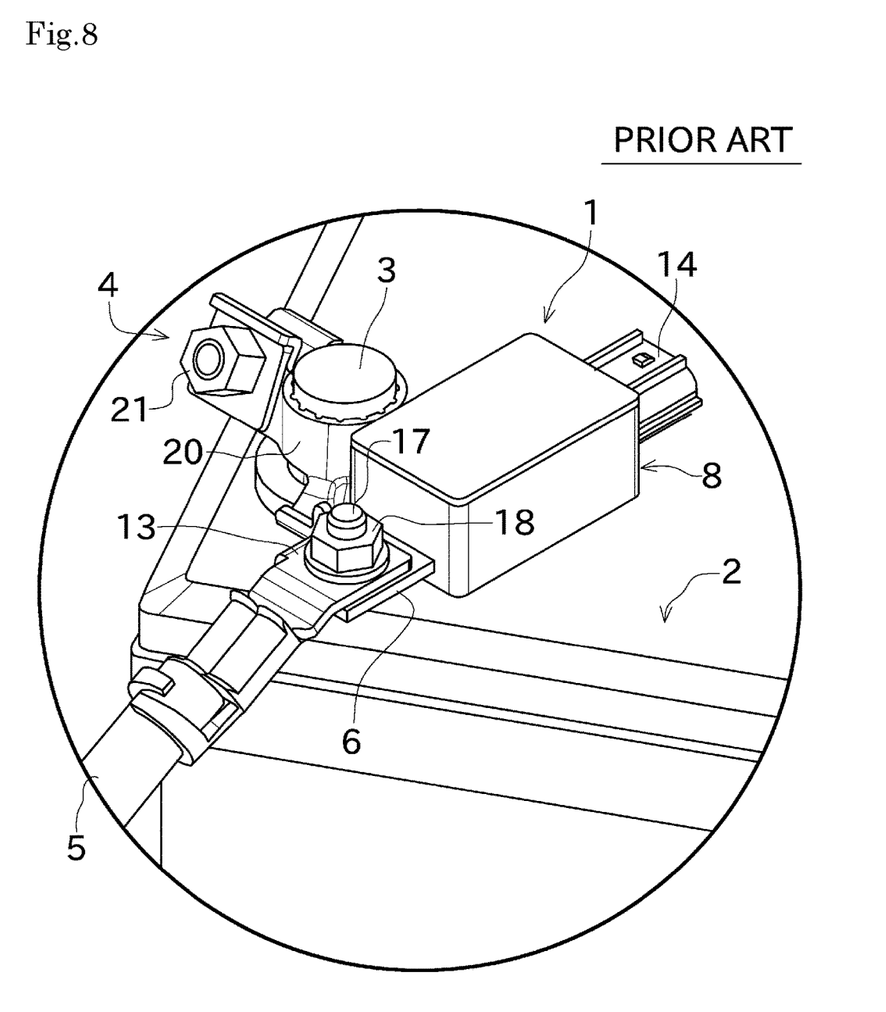
FIG. 8 A perspective view showing a conventional situation where the battery sensor is mounted to a battery.
Figure 9:
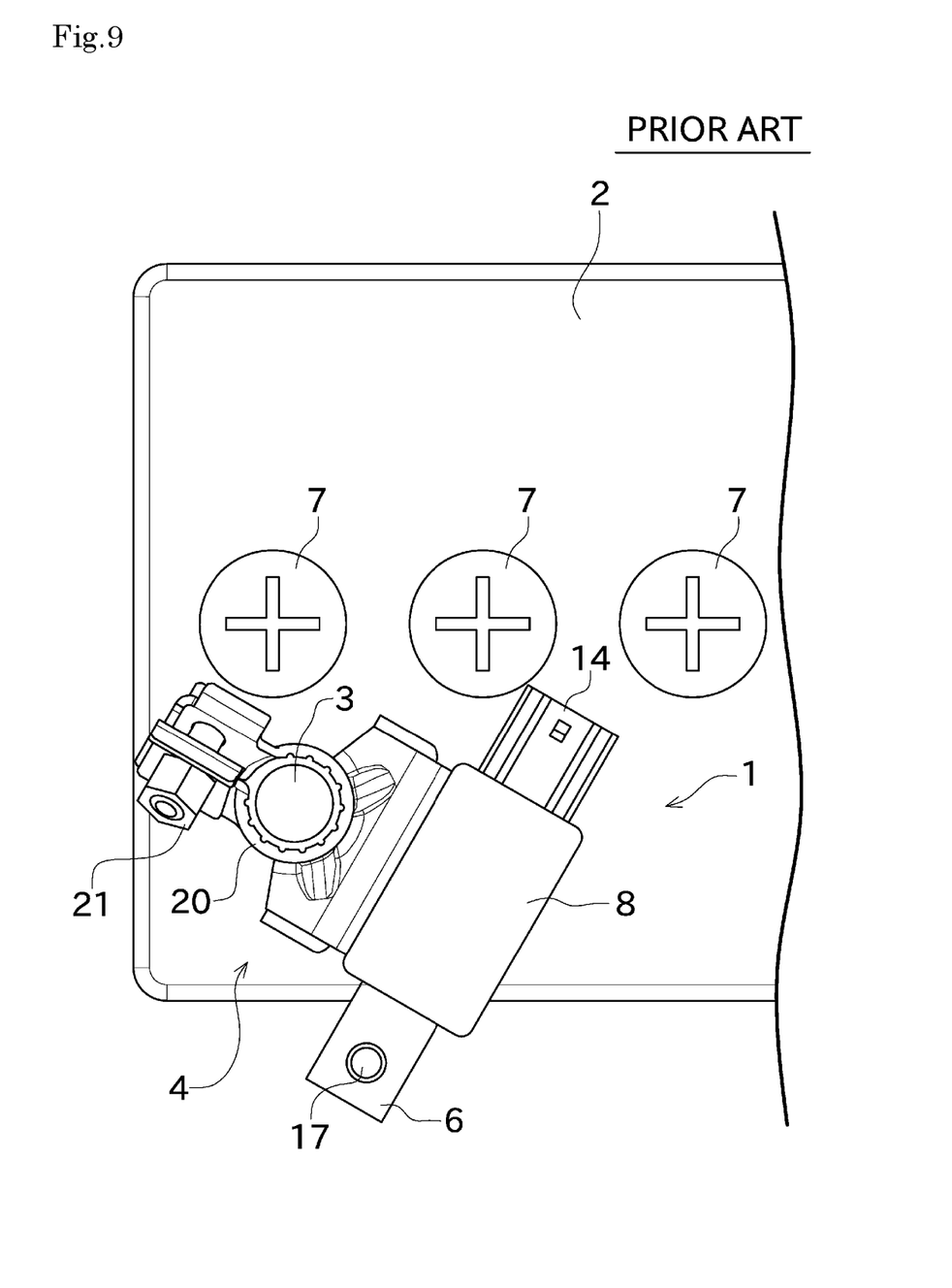
FIG. 9 A plan view showing a conventional situation where the battery sensor is mounted to a battery.

The conventional battery sensor will be briefly described with reference to FIGS. 8 and 9. As shown in FIGS. 8 and 9, the conventional battery sensor 1 includes a battery post terminal 4, a harness connecting part 6 and a casing 8.

The battery post terminal 4 is mounted to a battery post 3 included in a battery 2. The battery post terminal 4 is made of a metal plate formed by a stamping or bending process. As shown in FIGS. 8 and 9, the battery post terminal 4 has a battery post connecting part 20 being in a substantially cylindrical shape. When the battery sensor 1 is mounted to the battery 2, a tightening bolt 21 is tightened under a state where a battery post connecting part 20 receives the battery post 3 therein, so that the battery post connecting part 20 bites into a peripheral surface of the battery post 3. As a result, the battery sensor 1 is (electrically and mechanically) connected to the battery post 3.

A harness connecting part 6 is connected to a harness 5 that is connected to a load (not shown). The harness connecting part 6 has a bolt (stud bolt) 17. On the other hand, the harness 5 has, in its end portion, a terminal 13 (FIG. 8). As shown in FIG. 8, the bolt 17 of the harness connecting part 6 is received through the terminal 13, and additionally a nut 18 is tightened to the bolt 17. This structure, which enables the harness 5 to be (electrically and mechanically) connected to the harness connecting part 6.

The casing 8, having a box-like shape, is generally made of a synthetic resin. The circuit board (not shown) having an electric circuit for detecting a state of the battery 2 is provided in the casing 8. The casing 8 has a connector 14 that outputs a result of the detection by the electric circuit. Though not shown in the drawings, a cable that outputs the result of the detection is connected to the connector 14.

As shown in FIG. 9, a vent plug (cap) 7 for replenishing battery liquid is arranged on the upper surface of the conventional battery 2. Therefore, the battery sensor 1 needs to be arranged so as not to overlap on the vent plug 7. If the battery sensor 1 is arranged so as to overlap on the vent plug 7, the vent plug 7 cannot be opened and thereby the battery liquid cannot be replenished.

FIG. 1 of Patent Document 4 shows a situation where a battery sensor is arranged so as not to overlap on a vent plug of the battery liquid.

PRIOR-ART DOCUMENTS

Patent Documents

Patent Document 1: Japanese Patent Application Laid-Open No. 2012-109098
Patent Document 2: Japanese Patent Application Laid-Open No. 2012-109099
Patent Document 3: Japanese Unexamined Patent Application Publication No. 2010-505103
Patent Document 4: Japanese Patent Application Laid-Open No. 2002-280083

SUMMARY OF THE INVENTION

PROBLEMS TO BE SOLVED BY THE INVENTION

FIG. 1 of Patent Document 4 shows that a situation where a main body casing of the battery sensor (current sensor) is arranged so as to protrude lateral to the battery. Such an arrangement of the battery sensor may cause interference with parts around the battery.

Particularly, in recent years, the number of parts in the engine room increases along with the trend of reducing capacity of an engine room size. Therefore, in order to improve the utilization efficiency of a space in the engine room, an innovation for the arrangement of the battery sensor is required.

For example, as shown in FIGS. 8 and 9, it is conceivable that the casing 8 of the battery sensor 1 is arranged above the battery 2. That is, the battery sensor 1 is arranged so that the casing 8 does not protrude lateral to the battery 2. This makes it less likely that the battery sensor 1 interferes with the parts around the battery 2. Therefore, the parts around the battery 2 can be densely arranged and then the utilization efficiency of a space in the engine room can be improved.

Meanwhile, a battery post 3 to which the battery sensor 1 is attached has a substantially cylindrical shape (or substantially truncated conical shape). Thus, the battery sensor 1, when mounting to the battery post 3, is likely to rotate around the battery post 3. Particularly, using an impact wrench or the like, when a tightening bolt 21 and a nut 18 is tightened, leads to shocks, and thereby the battery sensor 1 rotates around the battery post 3. Since the shocks caused by the impact wrench is considerably large, even if the mounting operator holds the battery sensor 1 by hands, rotation of the battery sensor 1 around the battery post 3 due to the shocks cannot be completely prevented.

Accordingly, the battery sensor 1 involves the problem having the difficulty of accurately mounting to the battery 2. Meanwhile, the innovation for improving the accuracy of mounting the battery sensor 1 to the battery 2 has not been conventionally made. This is because it has been considered that no hindrance occurs even when the position of the battery sensor 1 is slightly displaced. No problem occurs even when the battery sensor is mounted with a slight rotation around a battery post in a case of arranging a battery sensor as with, for example, shown in FIG. 1 of Patent Document 4.

As shown in FIG. 9, however, in case that a casing 8 of a battery sensor 1 is arranged above a battery 2, the position of the battery sensor 1 is merely slightly displaced (mounted in a state of a rotation around a battery post 3 in a condition of FIG. 9) so that the battery sensor 1 overlaps on a vent plug 7. Accordingly, the vent plug 7 cannot be opened.

The present invention has been made in view of the circumstances described above, and an object of the present invention is to provide a configuration for accurately mounting a battery sensor to a battery so as not to rotate around a battery post when the battery sensor is mounted to the battery post.

MEANS FOR SOLVING THE PROBLEMS AND EFFECTS THEREOF

Problems to be solved by the present invention are as described above, and next, means for solving the problems and effects thereof will be described.

In an aspect of the present application, a positioner for settling the position of a battery sensor mounted to a battery post of a battery is provided as follows. This positioner includes a sensor-fixing part for fixing the battery sensor, and a rotation-blocking part capable of coming in contact with a side surface of the battery.

The "side surface" of the battery mentioned herein means a side surface in which a surface having the battery post is regarded as an "upper surface" of the battery. That is, providing a rotation-blocking part capable of coming in contact with the side surface of the battery, can prevent the positioner from rotating around the battery post. Thus, fixing the battery sensor to this positioner can prevent the battery sensor from rotating around the battery post. This enables to accurately settle the position of the battery sensor to the battery.

Preferably, the above-described positioner is configured as follows. The sensor-fixing part includes a fitting section. The fitting section can be received at least a part of the battery sensor from a prescribed insertion direction and fits to the received battery sensor.

In such a configuration, the battery sensor can be easily fixed to a positioner merely by inserting the battery sensor into the fitting section and fitting to each other.

Preferably, in the above-described positioner, the sensor-fixing part further includes a lid section which comes in contact with the battery sensor fitted to the fitting section from the insertion direction.

Thus, providing the lid section can prevent the battery sensor from leaving from the fitting section. This enables to accurately fix the battery sensor to the positioner.

In the above-described positioner, it is preferable that the fitting section comes in contact with the battery sensor by a plurality of tapered ribs formed along the inserted direction.

In a configuration such that the fitting section comes in contact with the battery sensor by the ribs, rattling of the battery sensor fitted to the fitting section can be suppressed. Moreover, the ribs having a tapered shape bite into the battery sensor by press-fitting the battery sensor to the fitting section. This enables to firmly fix the battery sensor.

In the above-described positioner, it is preferable that the lid section comes in contact with the battery sensor by a plurality of bosses.

In a configuration such that the lid section comes in in contact with the battery sensor by a plurality of bosses, rattling of the battery sensor can be prevented when the lid section comes in contact with the battery sensor.

Preferably, the above-described positioner is configured as follows. That is, the sensor-fixing part includes a hinge part and a lock mechanism. The hinge part allows the lid section to connect to the fitting section integrally. The lock mechanism is configured such that the lid section is locked in a state of coming contact with the battery sensor.

In this manner, the fitting section and the lid section are connected to each other by the hinge part, and thereby they can be formed by integrally forming. Additionally, rotating the lid section and locking by the lock part enables to fix the battery sensor surely. Thus, the operation of fixing the battery sensor to the positioner can be performed firmly.

In the above-described positioner, the rotation-blocking part is preferably provided with at least one reinforcement rib.

That is, since an impact wrench or the like are used for mounting the battery sensor, it is expected that strong shocks are applied to the rotation-blocking part. Accordingly, providing at least one reinforcement ribs as described above prevents deformation of the rotation-blocking part.

In the above-described positioner, the at least one reinforcement rib can be preferably contact with a side surface of the battery.

In this manner, the position of the battery sensor is settled such that the at least one reinforcement rib come contact with the side surface of the battery. This can suppress rattling of the positioner and further enhance the accuracy of the position settlement of the battery sensor.

In another aspect of the present invention, a battery sensor assembly including the above-described positioner and a battery sensor fixed by the sensor-fixing part of the positioner is provided.

This battery sensor assembly includes the rotation-blocking part, so that mounting to the battery can be performed accurately.

EMBODIMENT FOR CARRYING OUT THE INVENTION

Next, an embodiment of the present invention will be described with reference to the drawings. FIG. 1 to FIG. 4 show a battery sensor assembly 10 according to an embodiment of the present invention.

Figure 1:
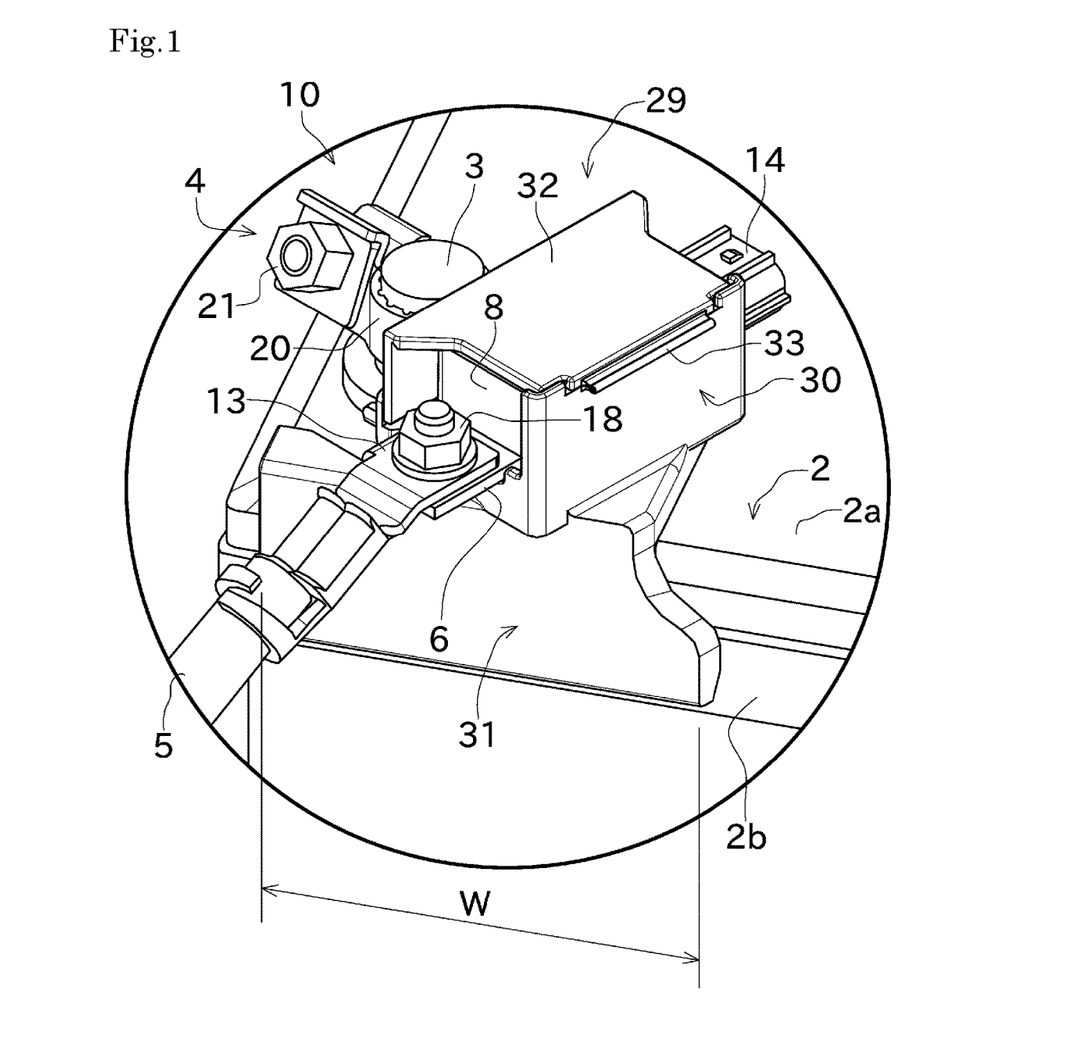
FIG. 1 A perspective view showing a situation where a battery sensor assembly is mounted to a battery according to an embodiment of the present invention.
Figure 2:
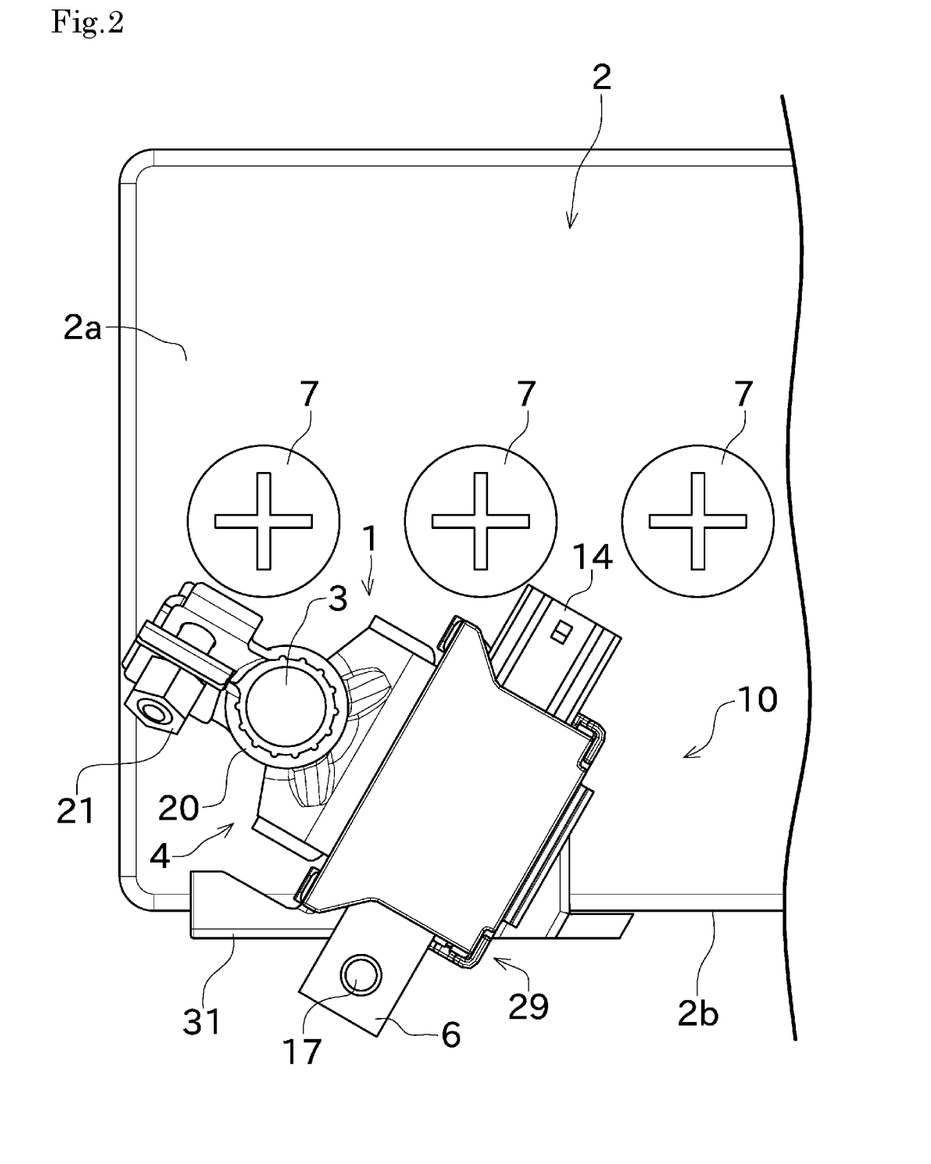
FIG. 2 A plan view showing a situation where a battery sensor assembly is mounted to a battery.

As shown in FIG. 1 and FIG. 2, the battery sensor assembly 10 is mounted to a battery post 3 of a battery 2. For convenience of the description, a surface where the battery post 3 is provided with the battery 2 is regarded as an upper surface 2a of the battery 2. Also, a surface where the battery 2 is substantially perpendicular the upper surface 2a is regarded as a side surface 2b of the battery 2.

Figure 3:
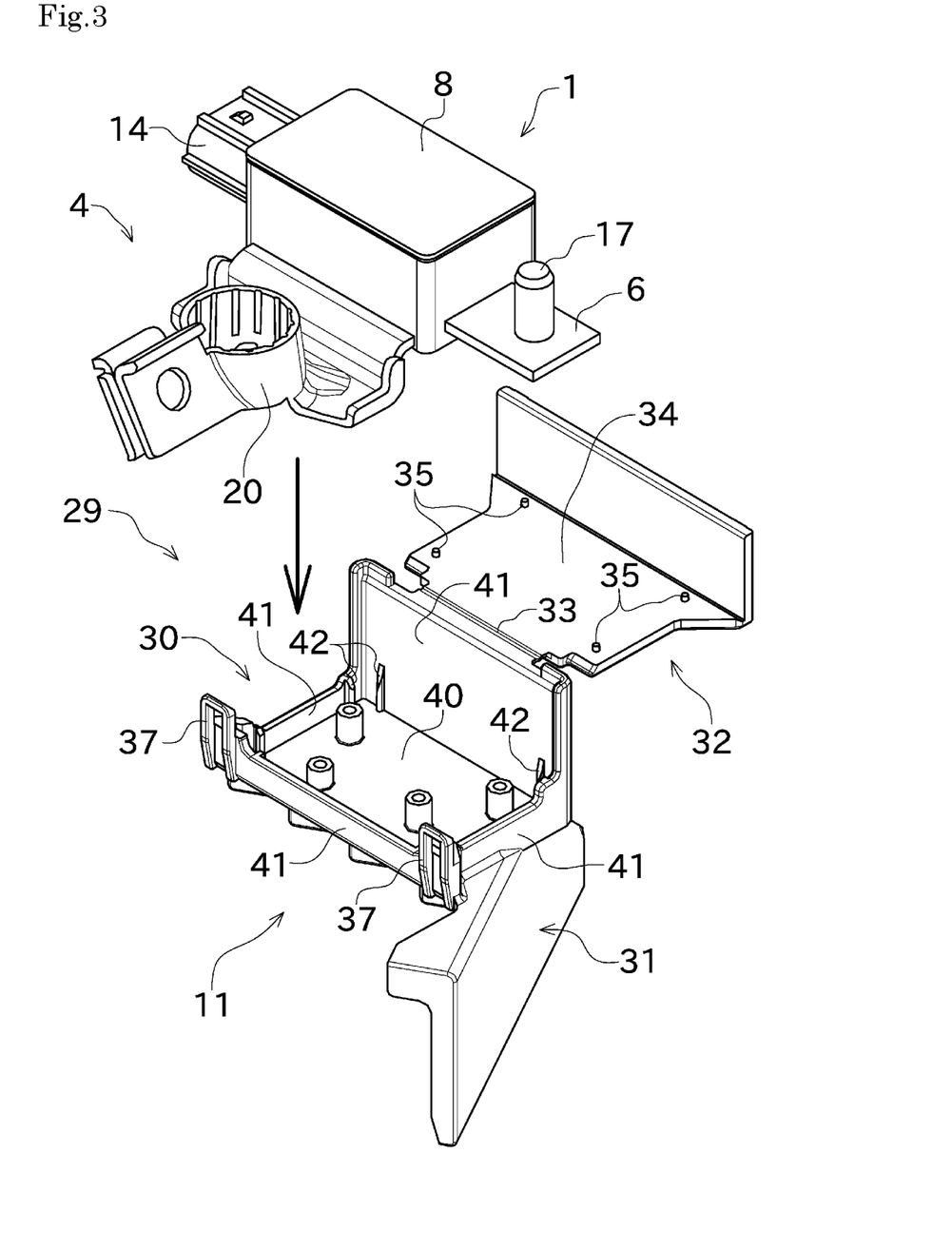
FIG. 3 A perspective view showing assembling of a battery sensor assembly.

As shown in a perspective assembly drawing of FIG. 3, the battery sensor assembly 10 includes a battery sensor 1 and a positioner 11.

The battery sensor 1 of this embodiment has the same configuration as the conventional battery sensor 1 which is already described with reference to FIG. 8 and FIG. 9. In the following description of this embodiment, elements already described will be denoted by the same corresponding reference signs as those of FIG. 8 and FIG. 9, and a description thereof may be omitted.

Figure 5:
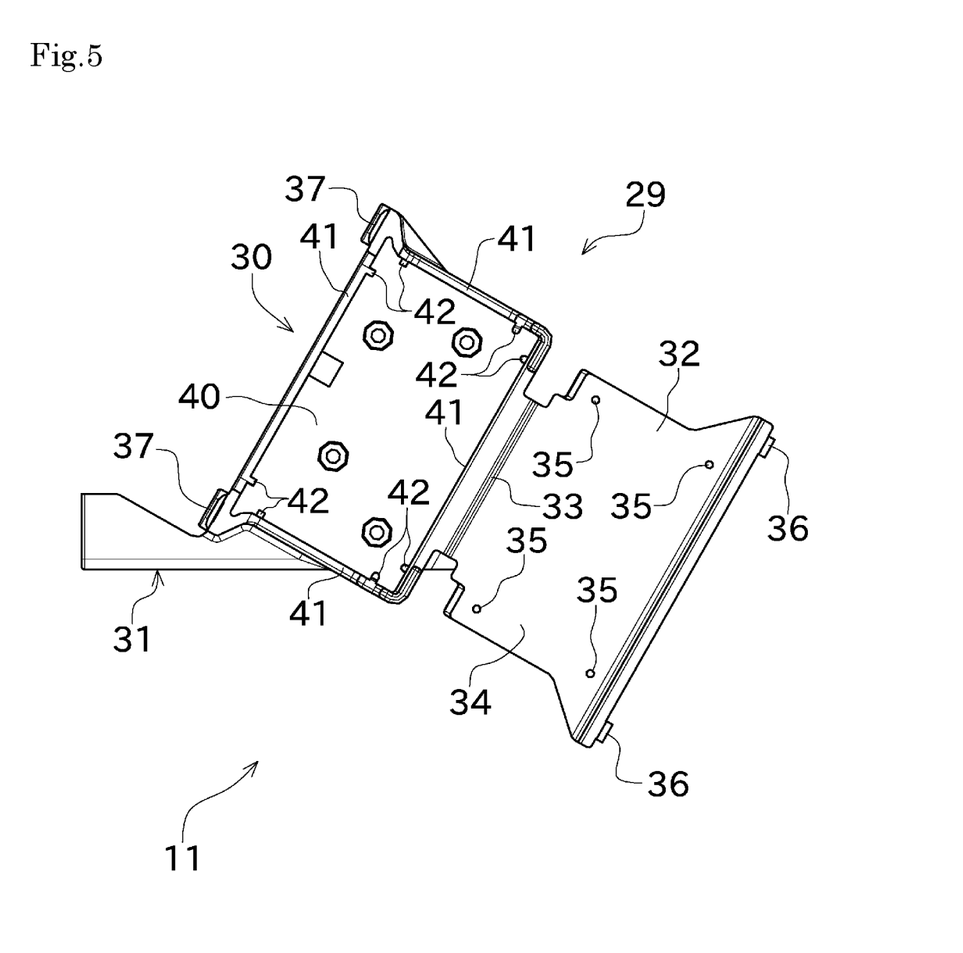
FIG. 5 A plan view of a positioner.
Figure 6:
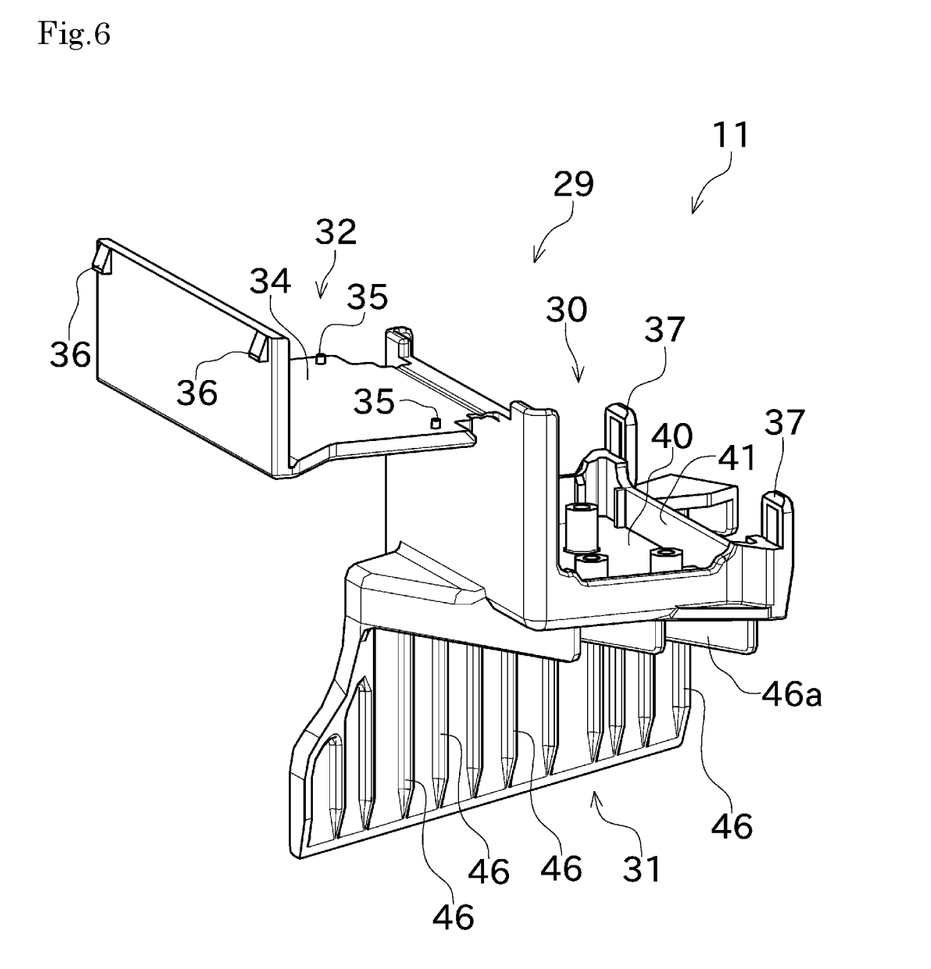
FIG. 6 A perspective view of a positioner.
Figure 7:
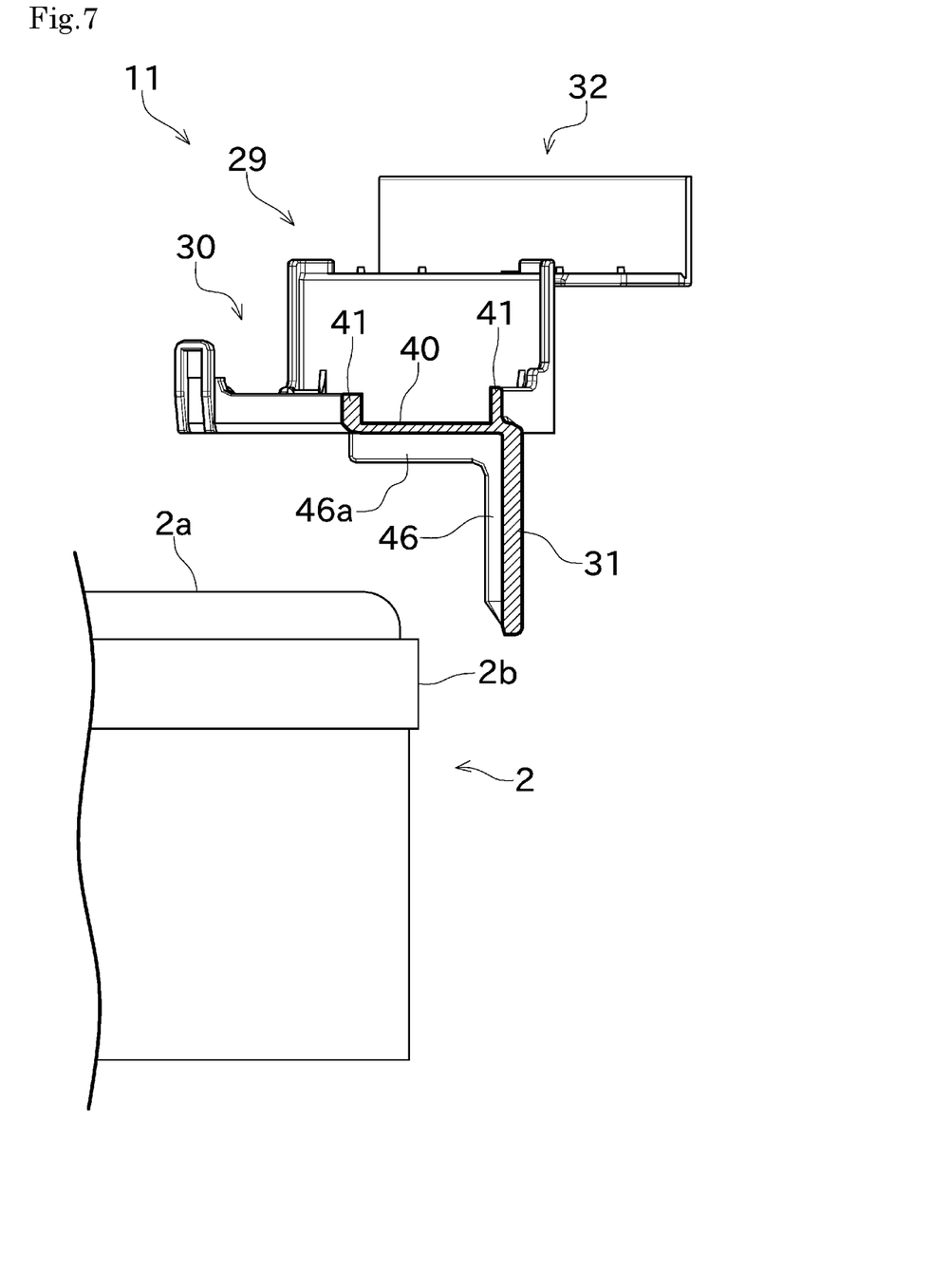
FIG. 7 A partial cross-sectional side view of a positioner.

A positioner 11 is made of a synthetic resin and integrally formed. In this embodiment, the positioner 11 and the battery sensor 1 are configured as separate pieces together as one unit. A configuration of the positioner 11 is shown in FIG. 5 to FIG. 7. The positioner 11 includes a sensor-fixing part 29 and a rotation-blocking part 31.

The sensor-fixing part 29 is configured such that the battery sensor 1 can be fixed to the positioner 11. In this manner, the battery sensor assembly 10 is configured by fixing the battery sensor 1 to the positioner 11.

Figure 4:
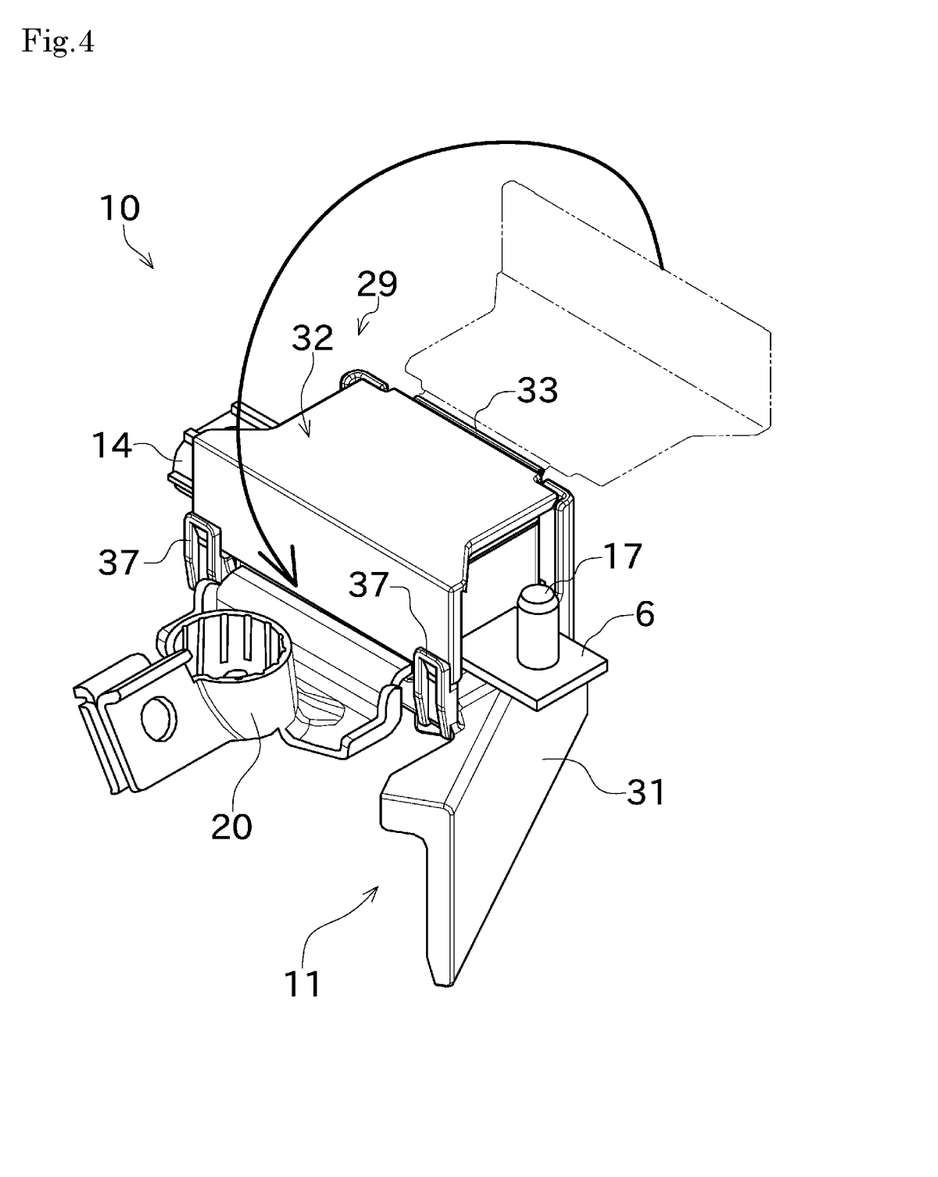
FIG. 4 A perspective view of a battery sensor assembly.

As shown in FIG. 1, FIG. 2, FIG. 4 or the like, in a state where the battery sensor 1 is fixed, each of a battery post terminal 4, a harness connecting part 6 and a connector 14 of the battery sensor 1 is configured to be exposed to outside the sensor-fixing part 29. Therefore, in a state where the battery sensor assembly 10 is configured (in a state where the battery sensor 1 is fixed to the positioner 11), the battery post terminal 4 can be connected to the battery post 3. In the same state where the battery sensor assembly 10 is configured, a harness 5 (FIG. 1) can be connected to a harness connecting part 6, or a cable (not shown) for outputting a detection result can be connected to a connector 14.

In this manner, the battery sensor assembly 10 is used in a state mounted to the battery 2 as it is (in a state where the battery sensor 1 is fixed to the positioner 11).

A rotation-blocking part 31 is configured so as to come in contact with a side surface 2b of the battery 2 when the battery sensor assembly 10 is mounted to the battery 2. More specifically, in a state where a battery post 3 is inserted in a battery post connecting part 20 of the battery sensor assembly 10 (in a state shown in FIG. 1 and FIG. 2), the rotation-blocking part 31 comes in contact with the side surface 2b of the battery 2.

As described above, the rotation-blocking part 31 comes in contact with the side surface 2b of the battery 2 and thereby the position of the battery sensor assembly 10 is settled to the battery 2. This can prevent the battery sensor assembly 10 from rotating around the battery post 3.

The following case is assumed in this embodiment. That is, the battery sensor 1 is fixed to the positioner 11 by an assembly operator at an assembly plant of a battery sensor assembly. Thus, a battery sensor assembly 10 is configured. Such a battery sensor assembly 10 is carried in an auto assembly plant or the like. In the auto assembly plant, the battery post terminal 4 of the battery sensor assembly 10 is mounted to the battery post 3 of the battery 2 of an automobile by a mounting operator.

When tightening a tightening bolt 21 or a nut 18 by the mounting operator, an impact wrench or the like may be used. When using the impact wrench or the like, shocks caused thereby leads to the rotation of the battery sensor assembly 10 around the battery post 3. If the battery sensor assembly 10 rotates by shocks generated by the impact wrench, fixing the battery sensor assembly 10 at the default position is difficult.

Particularly, as described in "problems to be solved by the invention", the battery sensor assembly 10 of this embodiment is assumed that a casing 8 of the battery sensor 1 is arranged above the battery 2 (in a state of FIG. 2). Therefore, only if the position of mounting the battery sensor assembly 10 is slightly displaced from the state of FIG. 2, the battery sensor assembly 10 overlaps on a battery liquid vent plug 7. Accordingly, the vent plug 7 cannot be opened.

In this respect, since the battery sensor assembly 10 of this embodiment includes a rotation-blocking part 31 having the above-described configuration, the position of the battery sensor assembly 10 is settled to the battery 2 by inserting a battery post 3 into a battery post connecting part 20. Even when shocks caused by an impact wrench are applied, the rotation of a battery sensor assembly 10 around the battery post 3 can be prevented. This enables to accurately mount the battery sensor assembly 10 to the battery 2 by a mounting operator.

In a configuration of this embodiment, a situation in which the battery sensor assembly 10 overlaps on a battery liquid vent plug 7 can be surely prevented. Additionally, a position of the battery sensor assembly 10 is settled accurately and thereby a situation in which the battery sensor assembly 10 interferes with parts around the battery 2 (not shown) can be surely prevented.

Next, a configuration of a sensor-fixing part 29 of the positioner 11 will be described.

The sensor-fixing part 29 of this embodiment includes a fitting section 30, a lid section 32, a hinge part 33 and a lock mechanism (a lock pawl 36 and a lock part 37).

The fitting section 30 is configured so as to fit to a casing 8 of a battery sensor 1.

Specifically, the casing 8 of the battery sensor 1 in this embodiment, as shown in FIG. 3, has a substantially rectangular parallelepiped shape. On the other hand, the fitting section 30 has a substantially rectangular tube shape so as to receive at least a part of the casing 8 having the rectangular parallelepiped shape.

More specifically, as shown in FIG. 3 and FIG. 5, the fitting section 30 includes a bottom surface 40 having a substantially rectangular shape and side walls 41 that are perpendicularly arranged from each of four sides on the bottom surface 40. The fitting section 30 having a substantially rectangular tube shape is provided by the bottom surface 40 and four side walls 41.

In the above-described configuration, the casing 8 of the battery sensor 1 can be inserted in the fitting section 30 from a direction orthogonal to the bottom surface 40 of the fitting section 30 (a direction indicated by an arrow of FIG. 3). A direction where the casing 8 is inserted in the fitting section 30 (a direction indicated by an arrow of FIG. 3) may be referred to as "insertion direction" in the following description.

As shown in FIG. 3 and FIG. 5, four side walls 41 are provided with a plurality of ribs 42 respectively. Each of the ribs 42 is provided on the side walls 41 so as to protrude inside the fitting section 30, and has an elongated shape in the insertion direction. Each of the ribs 42 is configured to come in contact with a side surface of the casing 8 inserted in the fitting section 30 respectively. Each of the ribs 42 of the fitting section 30 comes in contact with the casing 8 inserted in the fitting section 30 and thereby the fitting section 30 is fitted to the casing 8.

Each of the ribs 42 has a portion in which moving toward the insertion direction (being close to the bottom surface 40) results in large protrusions. That is, each of the ribs 42 has a tapered-shape portion. In this manner, each of the ribs 42 has a tapered shape so that the casing 8 is guided by the taper and centered in the fitting section 30 when the casing 8 is inserted in the fitting section 30. In this state, further pressing the casing 8 in the insertion direction allows tapered ribs 42 to bite into an outer surface of the casing 8.

As a result, the casing 8 is firmly fixed to the fitting section 30, thereby rattling of the casing 8 in the fitting section 30 can be prevented.

As shown in FIG. 3 or the like, a hinge part 33 is configured to connect a fitting section 30 and a lid section 32. The hinge part 33 of this embodiment is a so-called thin-walled hinge (living hinge). Therefore, the fitting section 30 and the lid section 32 are integrally connected by the hinge part 33. As shown in FIG. 4, the lid section 32 can rotate around the hinge part 33 relative to the fitting section 30. As shown in FIG. 3 and FIG. 5, the lid section 32 has a ceiling surface 34. Rotating the lid section 32 results in a state of FIG. 4, so that the ceiling surface 34 of the lid section 32 is opposed to the bottom surface 40 of the fitting section 30. This state of FIG. 4 is called as the "closed" state of the lid section 32.

As shown in FIG. 3 or the like, a plurality of bosses 35 is provided on the ceiling surface 34 of the lid section 32. The bosses 35 are provided as small protrusions having substantially cylindrical shapes. When the lid section 32 is closed in a state where the casing 8 is fitted to the fitting section 30 (in a state of FIG. 4), the bosses 35 come into contact with the upper surface of the casing 8 from the insertion direction. Accordingly, the casing 8 is held down toward the bottom surface 40 side of the fitting section 30 by the bosses 35 of the ceiling surface 34.

Accordingly, "closing" the lid section 32 (being a state of FIG. 4) can prevent the casing 8 from falling out of the fitting section 30. Additionally, the casing 8 is held down by a plurality of bosses 35 and thereby rattling of the casing 8 can be suppressed effectively.

The above-mentioned lock mechanism includes a lock pawl 36 and a lock part 37. More specifically, as shown in FIG. 5 and FIG. 6, the lock pawl 36 is provided with the lid section 32. On the other hand, as shown in FIG. 5 and FIG. 6, the lock part 37 is provided with the fitting section 30. Being a closed state of the lid section 32 results in a configuration of the lock mechanism, in which the lock pawl 36 is engaged with the lock part 37 and the lid section 32 is locked with a closed state.

Thus, when assembling this battery sensor assembly 10, the casing 8 of the battery sensor 1 is inserted into the fitting section 30 of the positioner 11 and fitted each other (FIG. 3). The battery sensor 1 is fixed to the positioner 11 merely by closing the lid section 32 and fitting to the lock mechanism (the lock pawl 36 and the lock part 37) (FIG. 4). In a configuration of the positioner 11 of this embodiment, the battery sensor 1 can be easily fixed to the positioner 11.

As mentioned above, the positioner 11 of this embodiment is assumed to settle the position in a state where the casing 8 of the battery sensor 1 is arranged above the battery 2. Therefore, the positioner 11 of this embodiment is configured such that the sensor-fixing part 29 is positioned above the battery 2 when the battery sensor assembly 10 is mounted to the battery 2. More specifically, when the battery sensor assembly 10 is mounted to the battery 2, at least a part of bottom surface 40 of the fitting section 30 is arranged so as to overlap on an upper surface 2a of the battery 2. In this embodiment, as shown in FIG. 7, the bottom surface 40 of the fitting section 30 is arranged substantially in parallel with the upper surface 2a of the battery 2. This enables to settle the position of the casing 8 in a state where the casing 8 of the battery sensor 1 is arranged above the battery 2.

Next, a configuration of a rotation-blocking part 31 of the positioner 11 will be described.

As mentioned above, the rotation-blocking part 31 is configured so as to come into contact with the side surface 2b of the battery 2 in a state where the battery post 3 is inserted in the battery post connecting part 20 (a state shown in FIG. 1 and FIG. 2). This can prevent the battery sensor assembly 10 from rotating around the battery post 3.

When tightening a tightening bolt 21 or a nut 18, using an impact wrench or the like causes shocks thereof. Due to the shocks, it is expected that a large force is applied to a rotation-blocking part 31.

The rotation-blocking part 31 of this embodiment comes into contact with the side surface 2b of the battery 2 in a wide range so as to distribute the shocks.

For example, the positioner 11 of this embodiment has in a plate shape having a large width. The width W (shown in FIG. 1) of the positioner 11 is larger than that of the casing 8 of the battery sensor 1. In a state where the battery sensor assembly 10 is mounted to the battery 2, the rotation-blocking part 31 comes into contact with the side surface 2b of the battery 2 throughout the width W.

In the manner, the rotation-blocking part 31 of this embodiment has a wide width W, a portion of coming contact with the side surface 2b of the battery 2. This can distribute the shocks applied to the rotation-blocking part 31, which is caused by using the impact wrench or the like when tightening the tightening bolt 21 or the nut 18. This can prevent the shocks from concentrating to a particular region, and the positioner 11 from deforming or damaging.

As shown in FIG. 6, the rotation-blocking part 31 has a plurality of reinforcement ribs 46. Each of the reinforcement ribs 46 is formed so as to protrude toward the side surface 2b of the battery 2. As shown in FIG. 7, each of the reinforcement ribs 46 has an elongated shape along a direction perpendicular to the bottom surface 40 of the fitting section 30. As shown in FIG. 6, the plurality of reinforcement ribs 46 is formed side by side in a direction perpendicular to a longitudinal direction thereof (in a width direction of the rotation-blocking part 31).

In this embodiment, the reinforcement ribs 46 reinforce the rotation-blocking part 31 and thereby deformation of the rotation-blocking part 31 can be prevented even when using the impact wrench or the like for mounting. Thus, the battery sensor assembly 10 can be mounted to the battery 2 accurately.

Moreover, as shown in FIG. 7, each of the reinforcement ribs 46 is formed such that a longitudinal direction is in parallel with the bottom surface 40 of the fitting section 30 by changing the longitudinal direction in an upper end portion thereof. This portion is called a horizontal portion 46a of the reinforcement ribs 46. Accordingly, the reinforcement ribs 46 have a substantially L-like shape when seen along a direction parallel to the bottom surface 40 of the fitting section 30 and parallel to the rotation-blocking part 31 (shown in FIG. 7). As shown in FIG. 7, each of the horizontal portion 46a of the reinforcement rib 46 is connected to the bottom surface 40 of the fitting section 30.

As described above, the reinforcement ribs 46 of this embodiment have the L-like shape such that the bottom surface 40 of the fitting section 30 is connected to the rotation-blocking part 31. Therefore, the reinforcement ribs 46 have a function of reinforcing so as to maintain an angle that is formed by the rotation-blocking part 31 and the bottom surface 40 of the fitting section 30. This can prevent deformation such as an enlargement of the angle formed by the rotation-blocking part 31 and the bottom surface 40 of the fitting section 30 even when strong shocks are applied to the rotation-blocking part 31 by using the impact wrench or the like.

As described above, the reinforcement ribs 46 formed on the rotation-blocking part 31 protrudes toward the side surface 2b of the battery 2. Therefore, the rotation-blocking part 31 comes in contact with the side surface 2b of the battery 2 by the reinforcement ribs 46.

That is, the rotation-blocking part 31 of this embodiment has a wide width W and therefore it is difficult that the rotation-blocking part 31 is formed smoothly with good accuracy throughout the width thereof. Likewise, the side surface 2b of the battery 2 may not be a completely smooth surface. If the rotation-blocking part 31 and the side surface 2b of the battery 2 come in contact with each other through a "surface" thereof, the battery sensor assembly 10 is rattled due to a difficulty of adhesion between them. As a result, the accuracy of the position settlement cannot be obtained. Therefore, the rotation-blocking part 31 comes in contact with the side surface 2b of the battery 2 by the reinforcement ribs 46, as described above. The reinforcement ribs 46 come in contact with the side surface 2b of the battery 2 with a "line". This can prevent rattling of the battery sensor assembly 10 even when the side surface 2b is not a completely smooth surface. Accordingly, the accuracy of the position settlement of the battery sensor assembly 10 can be enhanced.

As described above, the positioner 11 of this embodiment includes the sensor-fixing part 29 for fixing the battery sensor 1 and the rotation-blocking part 31 capable of coming in contact with the side surface 2b of the battery 2.

In this manner, providing the rotation-blocking part 31 capable of coming in contact with the side surface 2b of the battery 2 can prevent the positioner 11 from rotating around the battery post 3. Thus, fixing the battery sensor 1 to the positioner 11 can prevent the battery sensor 1 from rotating around the battery post 3. Therefore, the position of the battery sensor 1 can be settled to the battery 2 accurately.

As described above, the sensor-fixing part 29 of the positioner 11 in this embodiment includes the fitting section 30. The fitting section 30 is configured to receive the casing 8 of the battery sensor 1 from a prescribed insertion direction and to fit to the received battery sensor 1.

In such a configuration, the battery sensor 1 can be easily fixed to the positioner 11 merely by inserting the battery sensor 1 into the fitting section 30 and fitting each other.

As described above, the fitting section 30 comes in contact with the battery sensor 1 by a plurality of tapered ribs 42 provided along an insertion direction.

In this manner, such a configuration, in which the fitting section 30 comes into contact with the battery sensor 1 by the ribs 42, can suppress rattling of the battery sensor 1 fitted to the fitting section 30. Moreover, according to the ribs 42 having a tapered shape, press-fitting the battery sensor 1 into the fitting section 30 makes the ribs 42 bite into the battery sensor 1. This enables to fix the battery sensor 1 firmly.

As described above, the sensor-fixing part 29 of this embodiment further includes a lid section 32 that comes in contact with the battery sensor 1 fitted to the fitting section 30 from the insertion direction.

Providing the lid section 32 can prevent the battery sensor 1 from leaving from the fitting section 30. This enables to fix the battery sensor 1 to the positioner 11 accurately.

As described above, the lid section 32 comes in contact with the battery sensor 1 by a plurality of bosses 35.

Such a configuration, in which the lid section 32 comes in contact with the battery sensor 1 by the plurality of bosses 35, can suppress rattling of the battery sensor 1 when the lid section 32 comes in contact with the battery sensor 1.

As described above, the sensor-fixing part 29 of this embodiment includes a hinge part 33 and a lock mechanism. The hinge part 33 allows the lid section 32 to be connected to the fitting section 30 integrally. The lock mechanism locks the lid section 32 in a state of coming in contact with the battery sensor 1 (in a state of closing the lid section 32).

The fitting section 30 is connected to the lid section 32 by the hinge part 33, and thereby they can be formed integrally. The lid section 32 is rotated and locked by the lock part, and thereby the battery sensor can be fixed surely. This enables to easily perform the operation of fixing the battery sensor 1 to the positioner 11.

The rotation-blocking part 31 of this embodiment includes the reinforcement ribs 46, as described above.

That is, it is expected that strong shocks are applied to the rotation-blocking part 31 due to a use of an impact wrench or the like when mounting the battery sensor 1. Therefore, providing the reinforcement ribs 46 prevents deformation of the rotation-blocking part 31.

As described above, in the positioner 11 of this embodiment, the reinforcement ribs 46 can come in contact with the side surface 2b of the battery 2.

In this manner, the position settlement, by which the reinforcement ribs 46 come in contact with the side surface 2b of the battery 2, can suppress rattling of the positioner 11. Then, the accuracy of the position settlement can be further enhanced.

As described above, the battery sensor assembly 10 of this embodiment includes the positioner 11 and the battery sensor 1 fixed by the sensor-fixing part 29 of the positioner 11.

The battery sensor assembly 10 having the rotation-blocking part 31 can be mounted to the battery 2 accurately.

Next, another embodiment of the present invention will be described.

In the battery sensor assembly 10 of the above-described embodiment, the battery sensor 1 and the positioner 11 are configured as separate pieces. Such a configuration can obtain an effect of the present invention merely by mounting the positioner 11 to the conventional battery sensor 1. That is, in the above-described embodiment, the conventional battery sensor 1 can be diverted as it is.

However, regardless of the above-described advantage, the battery sensor 1 and the positioner 11 are not necessarily configured as separate pieces.

Therefore, a configuration in which a battery sensor 1 is integrated with a positioner 11 can be considered as another embodiment of the present invention. The sensor-fixing part 29 of the above-described embodiment is not necessary when the battery sensor 1 is integrated with the positioner 11 from the beginning. Accordingly, another embodiment may be considered as a configuration in which a rotation-blocking part 31 is directly provided with the battery sensor 1 without the sensor-fixing part 29 of the above-described embodiment.

In another embodiment, a configuration, in which a rotation-blocking part 31 comes in contact with a side surface 2b of a battery 2 when a battery sensor 1 is mounted to the battery 2, can obtain a same effect as the above-described embodiment for enhancing the accuracy of the position settlement.

Although a preferred embodiment (and another embodiment) of the present invention has been described above, the above-described configuration may be modified, for example, as follows.

In the above-described embodiment, any configuration is adoptable as the sensor-fixing part 29 as long as it is able to appropriately fix the battery sensor 1. Therefore, a configuration of the sensor-fixing part 29 is not limited to that of the above-described embodiment. Kinds of variations are conceivable.

For example, in the above-described embodiment, the casing 8 of the battery sensor 1 is fitted to the fitting section 30 of the positioner 11, however, the casing 8 being fitted to the fitting section 30 is not limited to this. A configuration in which another portion of the battery sensor 1 is fitted to the fitting section 30 may be also acceptable.

Additionally, the lid section 32 can be omitted as long as the battery sensor 1 is fixed to the fitting section 30 with the sufficient strength.

A configuration, in which another method for fixing the battery sensor 1 to the sensor-fixing part 29, instead of fitting together, may be also acceptable.

The positioner 11 of the above-described embodiment is assumed that the position of the casing 8 of the battery sensor 1 is settled above the battery 2. However, the position of which the battery sensor 1 is settled by the positioner 11 is not limited to the above-described embodiment. For example, as described in a configuration of FIG. 1 of the Patent Document 4, a positioner 11 may be configured such that a casing 8 of a battery sensor 1 protrudes toward a lateral side of a battery 2 and thereby the position is settled.

A configuration of the positioner 11 is not limited to the above-described configuration of the embodiment, but may be changed as appropriate. The same applies to the battery sensor 1.

DESCRIPTION OF THE REFERENCE NUMERALS

1 battery sensor
2 battery
2*a* side surface of a battery
3 battery post
10 battery sensor assembly
11 positioner
29 sensor-fixing part
30 fitting section
31 rotation-blocking part
32 lid section

The invention claimed is:

1. A positioner for settling the position of a battery sensor, including a battery post terminal and a casing incorporating a circuit board having an electric circuit for detecting a state of the battery, and the battery sensor being mounted to a battery post of a battery, comprising:
   a sensor-fixing part for fixing the battery sensor; and
   a rotation-blocking part capable of coming in contact with a side surface of the battery;
   wherein the sensor-fixing part includes a fitting section and a lid section, the fitting section configured to be inserted at least a part of the battery sensor from a prescribed insertion direction and fitted to the inserted battery sensor, the lid section configured to come in contact with the battery sensor fitted to the fitting section from the insertion direction,
   wherein the fitting section comes in contact with the battery sensor by a plurality of tapered ribs formed along the insertion direction, and
   wherein the battery sensor and the sensor-fixing part are configured as separate pieces.

2. The positioner according to claim 1, wherein the lid section comes in contact with the battery sensor by a plurality of bosses.

3. The positioner according to claim 1, wherein the sensor-fixing part includes a hinge part and a lock mechanism, the hinge part configured to connect the lid section to the fitting section integrally, the lock mechanism for locking the lid section in a state of coming in contact with the battery sensor.

4. The positioner according to claim 1, wherein the rotation-blocking part include at least one reinforcement rib.

5. The positioner according to claim 4, wherein the reinforcement ribs are able to come in contact with the side surface of the battery.

6. A battery sensor assembly comprising: the positioner according to claim 1; and a battery sensor fixed by the sensor-fixing part of the positioner.

7. The positioner according to claim 1, wherein the sensor-fixing part includes a fitting section, wherein the fitting section is configured to allow insertion of at least a part of the battery sensor from a prescribed insertion direction and fitted to the inserted battery sensor.

* * * * *